(12) United States Patent
Shriver et al.

(10) Patent No.: US 9,364,352 B1
(45) Date of Patent: Jun. 14, 2016

(54) CONTROLLING CIRCUMFERENCE OF CONCENTRIC SPIRAL WIRES BY LENGTH OF CONTROL WIRE IN CONTROL TUBE

(71) Applicants: Edgar Louis Shriver, Aventura, FL (US); George Elmer Shriver, Beckley, WV (US)

(72) Inventors: Edgar Louis Shriver, Aventura, FL (US); George Elmer Shriver, Beckley, WV (US)

( * ) Notice: Subject to any disclaimer, the term of this patent is extended or adjusted under 35 U.S.C. 154(b) by 0 days.

(21) Appl. No.: 14/544,442

(22) Filed: Jan. 8, 2015

(51) Int. Cl.
| | | |
|---|---|---|
| *A61F 2/06* | (2013.01) | |
| *A61F 2/88* | (2006.01) | |
| *A61F 2/07* | (2013.01) | |
| *A61F 2/852* | (2013.01) | |
| *A61F 2/95* | (2013.01) | |

(52) U.S. Cl.
CPC . *A61F 2/885* (2013.01); *A61F 2/07* (2013.01); *A61F 2/852* (2013.01); *A61F 2/95* (2013.01); *A61F 2002/072* (2013.01); *A61F 2002/075* (2013.01); *A61F 2210/0019* (2013.01); *A61F 2210/0057* (2013.01); *A61F 2210/0066* (2013.01)

(58) Field of Classification Search
CPC ................ A61F 2002/011; A61F 2/95; A61F 2230/0091; A61F 2/82; A61F 2250/006; A61F 2/90; A61F 2250/0065; A61F 2/07; A61F 2/2436; A61F 2/966; A61F 2002/016; A61F 2002/075; A61F 2002/077; A61F 2002/82
See application file for complete search history.

(56) References Cited

U.S. PATENT DOCUMENTS

| | | | | | |
|---|---|---|---|---|---|
| 5,503,636 | A * | 4/1996 | Schmitt | ..... | A61F 2/90 606/194 |
| 5,755,708 | A * | 5/1998 | Segal | ..... | A61F 2/958 604/104 |
| 6,019,779 | A * | 2/2000 | Thorud | ..... | A61F 2/88 606/198 |
| 7,713,215 | B2 * | 5/2010 | Shriver | ..... | A61B 17/00234 600/585 |
| 2001/0003801 | A1 * | 6/2001 | Strecker | ..... | A61B 17/12022 623/1.11 |
| 2001/0004683 | A1 * | 6/2001 | Gambale | ..... | A61F 2/06 604/104 |
| 2009/0192592 | A1 * | 7/2009 | Asgari | ..... | A61F 2/82 623/1.39 |
| 2014/0200648 | A1 * | 7/2014 | Newell | ..... | A61F 2/966 623/1.11 |

* cited by examiner

*Primary Examiner* — Christopher D Prone
*Assistant Examiner* — Ann Schillinger

(57) ABSTRACT

Ends of an outer spiral and an inner spiral of similar dimensions but wound in opposite directions are joined to form a double spiral stent which may be covered to make it a stent graft. The dimensions are related by the formula of $C=(Lw-Ls)/N$ where C is circumference of the spiral, Lw the length of the wire, N the number of turns and Ls the length of the spiral. Thus when length of spiral (Ls) is increased and decreased by compression and stretching, circumference (C) inversely varies with Ls, as N and Lw do not change. Ls and thus C are controlled by a control wire in a control tube attached to the ends of the double spiral being changed either by screwing male threads on the control wire into and out of female threads in the control tube.

7 Claims, 2 Drawing Sheets

CONTROLLING CIRCUMFERENCE OF CONCENTRIC SPIRAL WIRES BY LENGTH OF CONTROL WIRE IN CONTROL TUBE

CROSS-REFERENCE TO RELATED APPLICATIONS

This is a new invention of a double spiral stent and stent graft and first inventor is the inventor of a prior art single spiral stent graft disclosed in U.S. patent application Ser. No. 13/694,529, titled "Suturing an Expanding Contracting Graft Tube in Artery Segment Previously Occluded".

FEDERALLY SPONSORED RESEARCH

Not Applicable

SEQUENCE LISTING OR PROGRAM

Not Applicable

BACKGROUND OF THE INVENTION

Field of the Invention

The field generally relates to means of increasing, decreasing and locking the size of spiral stents and stent grafts placed in the body percutaneously.

BACKGROUND OF THE INVENTION

Prior Art

| Number | Date | Inventor |
| --- | --- | --- |
| 3334629 | August 1967 | Cohn |
| 3494806 | February 1970 | Brumlik |
| 4503569 | March 1985 | Dotter |
| 4733665 | March 1988 | Palmaz |
| 4893623 | January 1990 | Rosenbluth |
| 5002563 | March 1991 | Pyka |
| 5163955 | November 1992 | Love et al. |
| 5197978 | March 1993 | Hess |
| 5662700 | September 1997 | Lazarus |
| 5810870 | September 1998 | Myers |
| 6264684 | July 2001 | Banas |
| 6652570 | November 2003 | Smith |
| 7131516 | June 2005 | Greenhalgh |
| 7713215 | May 2010 | Shriver |
| 7771422 | August 2010 | Shriver |
| 8400224 | April 2011 | Shriver |
| 8211160 | July 2012 | Garrison et al |
| 13/694529 | December 2012 | Shriver |

BACKGROUND OF THE INVENTION

Devices and Procedures

Medical devices are applied to the body to act on the body and the body will act on them but this does not mean such medical devices involve patenting any aspect of the body and this is the case with the device described herein. Millions of percutaneous transluminal angiographic (PTA) procedures are performed each year to treat occlusions, that are also called stenoses, in diseased coronary and peripheral arteries. The PTA procedure acts on an occluded/stenosed segment of an artery to open it so blood can flow through the previously occluded segment. The stenosis grows back at a rate that depends on many factors but across many conditions it returns to a sufficient extent to require another PTA in an average of 2½ years in 50% of cases. This restenosis may be delayed by placing any one of a variety of wire frameworks in the shape of an expandable tube called a stent to keep the artery propped open after the PTA. When a stent is added in a coronary artery the duration added to PTA alone is about 2½ years for a total duration of about 5 years until about 50% of occlusions/stenoses have grown back through the stent to re-instate the occlusion and require a repeat treatment so blood can flow. But in peripheral arteries where the legs are moving and the occlusions tend to be long, stents are likely to fracture, thus they add only marginally to the 2½ year duration of PTA treatment alone. Stent grafts were invented to provide a more flexible frame to avoid fracturing and a covering is added to resist re-stenosis through the frame. Such stent graft frames successfully avoid fracturing and their covers resist re-stenosis, but the stenosis tends to grow back around the stent graft ends in about the time that restenosis occurs through a bare stent thus a stent graft does not increase duration of treatment over that of a stent. This return of the stenosis around stent graft ends is called focal edge stenosis and occurs primarily at the proximal end. Though the exact causes are not well understood it is generally believed to involve blood flow dynamics and irritation to the artery wall which induces hyperplasia and rapid re-growth. The irritation may be rubbing, twisting or torsion, but only one means has been found to significantly reduce focal edge stenosis. That means is matching stent graft circumference and circumference of artery at landing sites in the previously occluded segment of artery. Unfortunately neither of the two common means of changing stent circumference is capable of achieving a stent circumference to match artery circumference. The most common means is a balloon inflated in the stent to increase its circumference. The result of this action is observed by the physician in a fluoroscopic X-ray image to determine when the stent and artery are the same size. In theory inflation is stopped when equal in size. But in practice the physician is looking at the artery segment that contains the stent and comparing it to the artery segment that does not contain the stent and it is not until the segment with the balloon and stent in it has overinflated enough for the physician to detect the difference that the physician stops increasing its size. Once this occurs, the balloon has increased the stent size to a greater circumference than that required for a match. After that, decreasing the balloon size does not decrease the stent circumference so the stent remains at the largest circumference the balloon reached even though the balloon decreases in size. Thus the desired match cannot be achieved once the balloon is over inflated. On average physicians overinflate by an average of about 20% before they recognize the difference in size. There was an experiment in which the amount of error was "over 20%" vs. "under 20%" difference in size and this was accomplished by sorting the cases after the fact to those under 20% and those over 20% larger than artery circumference. This was useful for determining that "under 20%" results in a significantly longer treatment duration than "over 20%" but provides no way of accomplishing the "under 20%" size before the fact. Another means a physician is provided to match circumference of stent graft and circumference of artery is by estimating the size of the artery before the stent graft is introduced into it. The type of stent used for this means of matching is one made of a nickel titanium compound and heat treated so it has a memory of a larger size that it will return to when heated to the temperature of the body. The delivery size is much smaller in circumference than the memory size. However the physician must estimate the memory size that will be needed. This is done by looking at the artery by fluoroscopic X-ray before the stent graft is introduced into the artery. Or ultra sound imaging may be substituted for fluoroscopic X-ray in an attempt to improve the estimate but this requires additional time and expertise and there are no data that indicate the extent to which this increases accuracy. The X-ray is an imprecise means of estimating and has not proven effective in bringing the error average to less than 20%. Another means of solving the error problem appears to be by providing a means of successive approximations by adjusting the stent graft size both up and down while the stent graft is in the artery under fluoroscopic X-ray examination. No stent graft currently provides the means of increasing and decreasing stent size in the artery. The present device is designed to increase and decrease in circumference a double spiral stent or stent graft by use of two somewhat different configurations. The stent or stent graft is designed to be increased and decreased in size while the stent/stent graft is in the artery where sizes can be directly compared by X-Ray fluoroscopy the physician uses to accurately compare the sizes of artery and stent/stent graft and adjust accordingly. This is unlike conventional stent grafts that do not provide any means to reduce the size once the physician has made it greater than artery size during the comparison. The present device provides, as does a prior art device by one of the inventors, to increase and decrease stent/stent graft size while it is in the artery. That device was revealed in U.S. Pat. No. 6,195,986 dated Aug. 19, 2013 titled "Suturing an Expanding, Contracting Graft Tube in Artery Segment Previously Occluded". That revealed a single spiral stent/stent graft in which the single spiral is rotated to increase and decrease its circumference and included in the device is a means of suturing the stent graft ends to the artery at landing sites. The present device discloses a double spiral stent/stent graft which include means of changing their length and thus increasing and decreasing their circumference while in the artery until the operator is satisfied with the match between circumference of artery and double spiral stent/stent graft which is then it is locked to the desired length and circumference.

Advantages

1. Stent or stent graft is preselected to be the approximate circumference and length for treating the previously occluded artery then introduced into the artery to be fine tuned by increasing and decreasing the circumference to that of the artery in which it is located, as observed with X-Ray fluoroscopy while in the artery.

2. The length of the double spiral frame of the stent/stent graft is controlled in order to increase and decrease the circumference of the stent/stent graft while in the artery and thus to match the artery circumference.

3. The shape of the double spiral stent/stent graft may be tapered to match the taper of the artery in which it is placed to improve the fit of double spiral stent/stent graft and artery throughout their length in common.

4. There are concentric inner and outer spirals of wire that have their ends joined to form the double spiral stent/stent graft and equal and opposite torsion is created in each and by changing their length and circumference that torsion is counteracted thus conferring no torsion to artery.

5. The same spiral frame of attached concentric spiral wires may be used as a bare double spiral stent or covered with a PTFE cover to create a double spiral stent graft.

6. Flexibility of a spiral is greater than that of other stent designs thus a spiral stent best resists fracturing.

7 Two means of varying length are provided in alternative configurations, one requiring balloons on concentric catheters, with heat treated indents and detents on a control wire in a control tube and a second with a turning arm for screwing male threads on the control wire into female threads in the control tube and in each alternative configuration locking length which also locks circumference.

| Key | |
|---|---|
| 1. | Outer spiral |
| 2. | Inner spiral |
| 3. | Double spiral stent graft |
| 4. | Clips |
| 5. | Control tube |
| 6. | Control wire |
| 7. | Guidewire |
| 8. | Cover |
| 9. | Double spiral stent |
| 10. | Distal balloon |
| 11. | Proximal balloon |
| 12. | Distal catheter |
| 13. | Proximal catheter |
| 14. | Clamp tube |
| 15. | Indents detents |
| 16. | Turning arm |
| 17. | Fluid line |
| 18. | Fluid port |
| 19. | Threads |
| 20. | Clamp holder |
| 21. | Clamp |
| 22. | Cooling balloon |
| 23. | Hangers |
| 24. | Holding flanges |

BRIEF DESCRIPTION OF THE DRAWINGS

FIG. 9 shows an inflated cooling balloon on the distal catheter with its fluid supply line and fluid port on distal catheter also showing fluid supply lines and fluid ports for distal balloon and proximal balloon on distal and proximal catheters.

DETAILED DESCRIPTION OF THE PREFERRED EMBODIMENTS

Having thus described the figures, methods and means in accordance with the present invention, they are now described with reference thereto. It should be understood that steps described for each process may be omitted or the order changed or performed simultaneously without deviating from the spirit or scope of the invention. It should be understood that a specific application situation involving a vessel, such as an artery may have somewhat different characteristics than another application with another vessel, whether artery, vein or other tubular structure of the body such as urethra or even skin and each application situation may require somewhat different dimensions, numbers in a plurality, angle of entry, or other invention characteristics. The following description of preferred embodiments should be read with reference to the drawings, in which the elements in different drawings are numbered in like fashion. The drawings, which are not necessarily to scale nor of exact shape, nor angle which varies with individual cases, thus depict or represent specific embodiments and are not intended to limit the scope of the invention. Examples of materials, construction, dimensions and manufacturing processes are provided for various elements but merely as a representation of current manufacturing practice which may change during the patent period.

Also, it is contemplated that any optional feature of the inventive variations described may be set forth and claimed independently, or in combination with any one or more of the features described herein. Reference to a singular item includes the possibility that there is a plurality of the same items present but not seen in the view being described. More specifically, as used herein and in the appended claims, the singular forms "a," "an," "said," and "the" include plural referents unless specifically stated otherwise. In many cases there is more than one of an element having a singular name and associated number key thus plural usage of a singular element is used to refer to "them" rather than "it" thus the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity. Although the foregoing invention has been described in detail for purposes of clarity of understanding, it will be obvious that certain modifications may be practiced within the scope of the appended claims. Those skilled in the art will recognize that many of the examples provided here have suitable alternatives which may be used now and in the future.

Figure 1A:
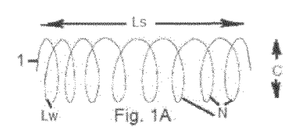
FIG. 1A is an outer spiral made of a length of wire (Lw), wound in a number (N) of turns in a clockwise direction with space between winds in a pre-selected circumference (C) and length of spiral Ls.

FIG. 1A shows outer spiral 1 having a proximal end, a distal end and therebetween a length of wire Ls, coiled in a spiral having N turns to create a spiral wire of circumference C and length Ls. Outer spiral 1 is made of a relatively flexible but strong material such as stainless steel or a preferred nickel titanium compound wound in a clockwise direction in a plurality of winds or turns N on an object like a mandrel with mandrel having a circumference that imparts that circumference to the outer spiral as its inner circumference. Outer spiral 1 retains its shape after removal from the mandrel but external force can change length (Ls). When the force exerted to compress or expand the length of outer spiral 1 (Ls) this also causes a change in circumference C. The dimensions will change in the relationship of the formula; $C=(Lw-Ls)/N$. The values of all variables are selected to obtain the circumference of the outer spiral that will be about the circumference of the artery in which outer spiral 1 is to be placed but that exact circumference (C) is obtained by the operator varying the length of outer spiral 1 (Ls) while in the artery.

Figure 1B:
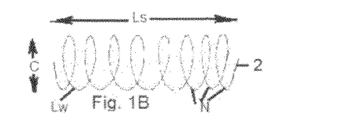
FIG. 1B is an inner spiral made of a length of wire, (Lw) of a smaller circumference (C) than circumference (C) of outer spiral of wire and wound in (N) turns in a counter clockwise direction with space between turns and a length of spiral (Ls) equal to the length of outer spiral (Ls).

FIG. 1B shows inner spiral 2 having a proximal end, a distal end and therebetween a spiral of wire. The inner spiral 2 has dimensions similar to those of outer spiral 1 being a length of wire Lw, a number of turns N, a length of spiral Ls and a circumference Cs. Outer spiral 2 is made of the same material as outer spiral 1, but is wound in a counter-clockwise direction in a plurality of winds or turns (N) on an object like a mandrel. The outer circumference of inner spiral 2 is made slidably smaller than the inner circumference of outer spiral 1 and other dimensions are such as to allow the distal end of inner spiral 2 to be attached to the distal end of outer spiral 1 and the proximal end of inner spiral 2 to be attached to the proximal end of outer spiral 1. Outer spiral 1 retains its shape after removal from the mandrel unless changed by external force. When the force exerted on outer spiral 1 is such as to compress or expand the length of spiral Ls, the circumference (C) will change in the relationship of the formula: $C=(Lw-Ls)/N$. Since N and Lw remain the same when length is changed, circumference (C) is the only variable (varies inversely with) that changes when length of spiral (Ls) is increased and decreased.

Figure 2A:
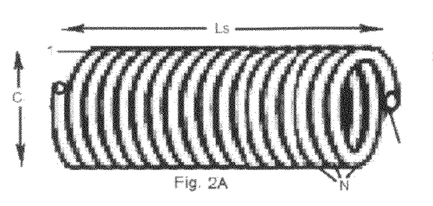
FIG. 2A is an outer spiral shown as wire wound in a clockwise direction with space between winds reduced to a minimum by compression thus decreasing length of spiral Ls and increasing circumference C.

FIG. 2A shows outer spiral 1 with the space between the plurality of winds pressed together by pushing ends which increases the circumference (C) (not shown to scale) and shortens the length of miter spiral 1 (Ls). It also creates torsion for return to the original shape in which outer spiral 1 was made.

Figure 2B:
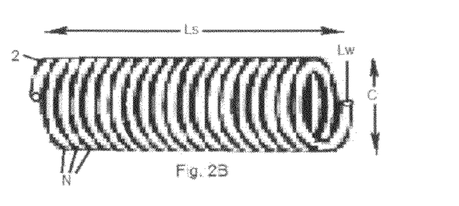
FIG. 2B is an inner spiral shown as wire wound a smaller circumference in a counter-clockwise direction with space between winds reduced to a minimum by compression thus decreasing length of spiral Ls and increasing circumference C.

FIG. 2B shows inner spiral 2 with the space between the plurality of winds pressed together by pushing ends which shortens the length of inner spiral 2 (Ls) and increases the circumference (C) (not shown to scale). It also creates torsion for inner spiral 2 to return to the original shape in which it was made. To equalize the torsion of inner spiral 2 and outer spiral 1 the wire diameter used in each may be different to compensate for the difference in torsion due to the difference in circumference of outer spiral 1 and inner spiral 2.

Figure 3A:
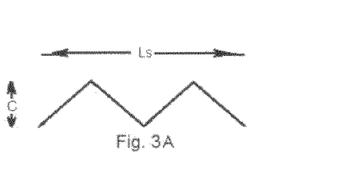
FIG. 3A shows a diagrammatic representation of two turns of a spiral wire spaced widely apart with circumference C and length of spiral Ls

FIG. 3A shows a diagrammatic representation of two turns of a spiral spaced widely apart with circumference (C) and length of spiral (Ls). This shows the wire having a fairly acute diagonal. It may be wound with this diagonal or pulled to this diagonal after winding has made the turns closer together.

Figure 3B:
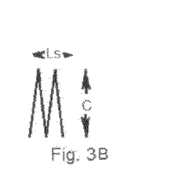
FIG. 3B shows a diagrammatic representation of the same two turns of a spiral spaced closer together than in FIG. 3A with an increased circumference C and decreased length of spiral Ls with respect to what is shown in FIG. 3A.

FIG. 3B shows a diagrammatic representation of the same two turns of a spiral spaced closely together. This increases circumference C and decreases length of spiral Ls with respect to what is shown in FIG. 3A. The fairly acute diagonal has been translated to almost a right angle. The number of turns (N) and length of wire (Lw) remain the same but the circumference is increased because the circumference now has a diameter of a wire at almost a right angle whereas that wire was at an acute angle as shown in FIG. 3A before the compression of turns was depicted in FIG. 3B.

Figure 3C:
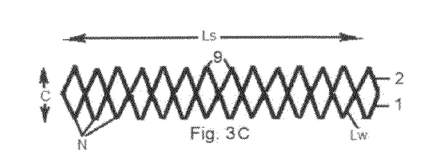
FIG. 3C shows a diagrammatic view of the inner spiral located concentrically in the outer spiral with distal ends of outer spiral and inner spiral attached and proximal ends of outer and inner spirals attached to make a double spiral stent.

FIG. 3C shows inner spiral 2 slidably located inside outer spiral 1 with the distal wire end of outer spiral 1 and distal wire end of inner spiral 2 attached together and the proximal wire end of outer spiral 1 and the proximal wire end of inner spiral 2 attached together. This attachment joins inner spiral 2 and outer spiral 1 in spiral stent 9. By attaching the ends whatever torsion exists to return to original size is generated in outer spiral 1 is counteracted by the torsion in oppositely wound inner spiral 2.

Figure 3D:
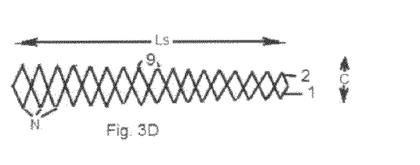
FIG. 3D shows a diagrammatic view of a tapered inner spiral located concentrically in a tapered outer spiral with distal ends of outer spiral and inner spiral attached and proximal ends of outer and inner spirals attached to make a tapered double spiral stent.

FIG. 3D shows inner spiral 2 tapered from proximal end to distal end and outer spiral 1 tapered from proximal end to distal end and distal end of outer spiral 1 and distal wire end of inner spiral 2 attached together and the proximal wire end of outer spiral 1 and the proximal wire end of inner spiral 2 attached together. This attachment joins the tapered inner spiral 1 and tapered outer spiral 2 In spiral stent 9 which is also tapered. The taper is obtained during manufacture by winding outer spiral 1 and inner spiral 2 on a tapered mandrel. The circumference (C) of the tapered double spiral stent 9 is the average circumference from the large proximal end to the small distal end. The amount of tapering is such as to match the tapering of the artery in which the tapered double spiral stent is intended for use. The tapered double spiral stent may have a tapered cover 8 described and shown in FIG. 4B and placed between outer spiral 1 and inner spiral 2 or outside outer spiral 1. Cover 8 is not shown in FIG. 3D, but is in FIG. 4B.

Figure 4A:
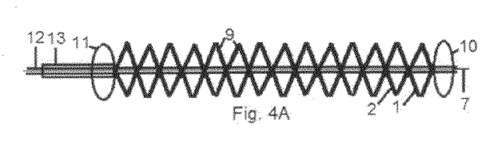
FIG. 4A shows the spiral stent with proximal balloon on proximal catheter and distal balloon on distal catheter, both balloons being placed just outside the proximal and distal ends of the spiral stent.

FIG. 4A shows distal balloon 10 mounted on distal catheter 12 inflated just distal to the distal end of spiral stent 9 and proximal balloon 11 mounted on proximal catheter 13 inflated just proximal to the proximal end of spiral stent 9. Distal catheter 12 is slidably received within proximal catheter 13 and the operator may move distal balloon 10 closer to proximal balloon 11 by moving the catheters thus decreasing the spiral length (Ls) and therefore increasing the circumference (C) of double spiral stent 9. The operator adjusts the balloons to the size of the artery by inflating and deflating them as she is also drawing together or pushing apart the distal and proximal balloons to control the spiral length and thus the circumference. The maximum length of double spiral stent 9 (Ls) is used during delivery to the previously occluded segment of artery then double spiral stent 9 is changed to the length (Ls) that produces a circumference about equal to that of the previously occluded artery segment. Also shown is guidewire 7 which is a pre-existing device not part of the device revealed here but shown to demonstrate how the present device is advanced on a guidewire in the normal manner in an artery to the segment of artery that was previously occluded.

Figure 4B:
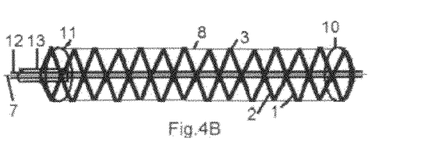
FIG. 4B shows the double spiral stent with a cover making it a double spiral stent graft and with proximal balloon on proximal catheter engaging proximal end of double spiral stent graft and distal balloon on distal catheter engaging distal end of double spiral stent graft.

FIG. 4B shows distal balloon 10 mounted on distal catheter 12 inflated within the distal end of double spiral stent graft 3. Cover 8 is a tube made of a material such as polytetrafluoroethelyne (PTFF) and this is an alternative configuration that converts spiral stent 9 into double spiral stent graft 3. Cover 8 is shown located between outer spiral 1 and inner spiral 2. In an alternative configuration cover 8 is placed outside outer spiral 1 but this configuration is not illustrated in a figure. Cover 8 resists re-growth of the occlusion or stenosis back through the open frame of double spiral stent 9. It is known that restenosis often occurs around the edge of stent grafts, especially the proximal edge. It has been found that making the circumference of the stent graft and the artery match slows this focal edge stenosis restenosis and making that match is a purpose of making a double spiral stent 9 and double spiral stent graft 3 that increase and decrease in circumference in the artery, allowing the operator to obtain the match by successive approximations. Drugs may be added to cover 8 to inhibit re-growth of the occlusion thus providing longer term inhibition than is provided by a drug eluting balloon. Proximal balloon 11, mounted on proximal catheter 13 is shown inflated in the proximal end of double spiral stent 3. Inflating balloons at these locations or any non-adjacent locations engages double spiral stent 3 so operator can move distal catheter 12 which is slidably received within proximal catheter 13 and thereby move distal balloon 10 closer to or farther from proximal balloon 11 thus increasing or decreasing the length and thereby the circumference of double spiral stent graft 3. Since changing length of spiral stent graft 3 also changes the circumference of spiral stent graft 3 the balloons may require more or less inflation fluid to retain engagement with double spiral stent graft 3 and these adjustments are made until operator judges the circumference (C) matches the circumference of the artery in which double spiral stent graft 3 is located after operator has advanced it to that location on pre-existing guidewire 7. The locations of distal balloon 10 and proximal balloon 11 inside double spiral stent graft 3 appears to provide a better grip of the proximal and distal ends of double spiral stent graft 9 than the location just proximal and distal to the ends of double spiral stent 3. But the operator can inflate distal balloon 10 and proximal balloon 11 at any other non-adjacent locations to obtain sufficient leverage to accomplish lengthening or shortening of the entire length of double spiral stent graft 3. It is obvious that what is said for double spiral stent graft 3 is equally applicable to double spiral stent 9.

Figure 5:
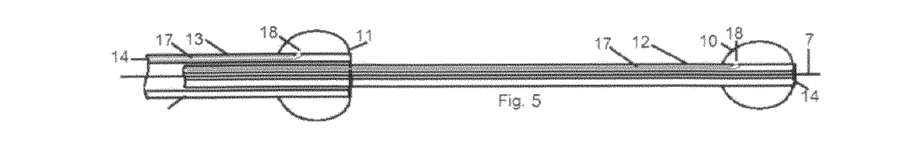
FIG. 5 shows proximal and distal balloons on proximal and distal catheters with fluid supply lines in walls of catheters and fluid ports opening to balloons

FIG. 5 shows details of distal catheter 12 slidably received in proximal catheter 13 and fluid lines 17 in the walls of distal catheter 12 and proximal catheter 13 with fluid ports 18 leading to distal balloon 10 and proximal balloon 11. It is not know whether or not spiral stent 9 or stent graft 3 will retain the length (Ls) and circumference (C) operator achieves by adjusting them with distal balloon 10 and proximal balloon 11. If not, means of retaining length (Ls) and circumference (C) are needed and provided by a control wire in a control tube as described in association with the following Figs.

Figure 6:
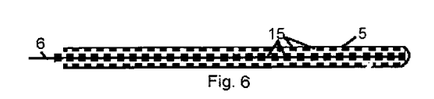
FIG. 6 shows a control wire with detents and indents along its length slidably received in a control tube having matching detents and indents and control wire is completely overlapping the control tube thus having the shortest possible combined length.

FIG. 6 shows control wire 6 having a distal end and a proximal end with a length of wire therebetween, made of a relatively stiff metal such as a nickel titanium compound and having a plurality of indents and detents 15 along its length. Control tube 5, has a distal end and proximal end with a length of hollow tube therebetween made of the same material as control wire 6 and having indents detents 15 along interior length of hollow tube that match indents detents 15 on control wire 6.

Control tube 5 is shown in a cross-section view in order to show inside hollow tube 5. Control tube 5 is shown slidably receiving control wire 6 and indents detents 15 on control wire 6 and control tube 5 do not touch when below body temperature. Control tube 5 is made of a relatively inflexible metal such as a nickel titanium compound. Either or both control tube 5 and control wire 6 are heat treated to permanently change their memory for size as a function of temperature and thus engage each other with indents detents 15 when reaching body temperature. Heat treated nickel titanium compound has a characteristic of returning to a preformed shape on warming to body temperature. It is obvious that both or either control wire 6 and control tube 5 can be heat treated to accomplish this action and that the plurality of indents 15 and detents 16 match in control tube 5 and control wire 6. When reaching body temperature, control tube 5 permanently decreases in size so indents detents 15 fit between indents detents 15 on control wire 6 thus locking control tube 5 and control wire 6 together permanently at their combined overlapping length while body temperature is maintained.

Figure 7A:
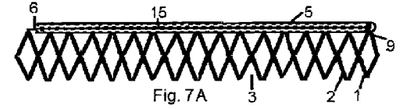
FIG. 7A shows a control tube with control wire inside attached to and located outside the double spiral stent for ease of viewing.
Figure 7B:
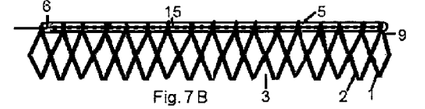
FIG. 7B shows a control tube with control wire inside located attached to and located inside the double spiral stent which is its preferred alternative location.

FIG. 7A shows distal end of control tube 5 attached to the one or more turns of distal end of double spiral stent 9. Control wire 6 has proximal end attached to one or more winds of double spiral stent 9 on proximal end. Control wire 6 and control tube 5 are shown attached on the outer circumference of double spiral stent 9 primarily to allow the viewer to have an unobstructed view of indents detents 15 shown inside the cross-section view of control tube 5. The preferred location for attachment of control tube 5 and control wire 6 is inside double spiral stent 9 as shown in FIG. 7B. However the site of attachment can be on the inner circumference or the outer circumference of spiral stent 9. It is obvious that double spiral stent 9 may be double spiral stent graft 3 though no figure is provided to show cover 8 for this alternative configuration.

FIG. 7B shows control wire 6 and control tube 5 attached on the inner circumference of inner-outer pair 9. This is the preferred alternative configuration but placement on the outer circumference makes indents detents 15 more easily seen. In both FIGS. 7A and 7B control wire 6 and control tube 5 are completely overlapping making their combined overlapped length the minimum they can achieve.

Figure 7C:
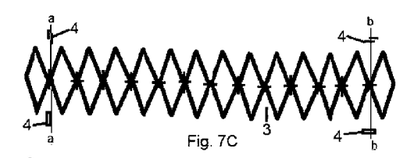
FIG. 7C shows loops of wire called clips for holding outer loop and inner loops together at points where they cross and clips are shown in cross section views in vertical and horizontal directions.

FIG. 7C shows an alternative configuration in which clips 4 are placed to hold together outer loop 1 and inner loop 2 at points where they cross. The clips are made of loops of wire twisted slightly so their end are not abutting but lie side-by-side. This is shown at cross sections "a" and "b" in two cross sectional views, one when clip is placed vertically on junction where outer loop 1 and inner loop 2 cross and the other shown when placed horizontally on junctions. Clips 4 may also be placed in both directions at a junction point where outer loop 1 and inner loop 2 cross. Clips 4 are made of a material like a nickel titanium compound and may be heat treated or not in alternative configurations. In the heat treated configuration they are made to shrink when reaching body temperature. The shrinking causes clips to close tightly on the junction of outer loop 1 and inner loop 2 while before reaching body temperature they allow the junction to move freely. This period may be extended by use of cooling balloon 22. Use of clips 4 causes spiral stent 3 to remain in the configuration the operator places it when cooling is removed from the body allowing the heat treated clips 4 to hold the junctions in the positions they are in. It may be noted that this also stiffens spiral stent 3 so it is not as flexible as in the configuration where clips 4 are not heat treated or not used.

Figure 8:
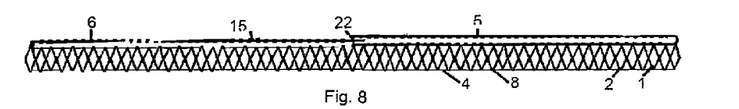
FIG. 8 shows control wire with minimal overlap with control tube thus producing the minimum circumference of spiral stent which is used for delivery into the artery.

FIG. 8 shows control wire 6 and control tube 5 attached as in FIG. 7A but on the inner circumference of spiral stent 9. Control wire 6 and control tube 5 are shown with their combined length the maximum they can achieve. This represents the maximum length (Ls) and minimum circumference (C) of spiral stent 9 and this is the configuration used during delivery of spiral stent 9 to the previously occluded site where it is to have circumference (C) increased by operator manipulating proximal balloon 11 and distal balloon 10. Detents indents 15 on control wire 6 and control tube 5 allow free increase and decrease in overlap until body heat causes heat treatment to take effect and this causes engagement of indents detents 15 on control wire 6 and in control tube 5 thus locking the combined length of non-overlapped control wire 6 and control tube 5 at the length selected by the operator. The operator observes the circumference (C) of spiral stent 9 or double spiral stent 3 by X-Ray fluoroscopy and compares it to the circumference of artery in order to obtain an accurate match of circumferences at which time the operator locks control tube 5 and control wire 6 by removing cooling fluid from balloons and allowing body heat to have its effect on the heat treated nickel titanium parts thus permanently establishing circumference (C) and length (Ls).

FIG. 9 shows a detail view of what is shown in FIG. 5 with the addition of cooling balloon 22 mounted on distal catheter 12. An additional fluid line 17 and additional fluid port 18 are included in the wall of distal catheter 12 for cooling balloon 22. Cooling balloon 22, as well as distal balloon 10 and proximal balloon 11 can have normal inflation fluid or chilled inflation fluid or liquid nitrous oxide passed through fluid lines to control the point at which body warmth will permanently change the heat treated size of adjacent heat-treated nickel-titanium compounds. Pre-existing guidewire 7 is shown in distal catheter 12 for advancing either double spiral stent 3 or spiral stent 9 to the segment of previously occluded artery in which it is placed for accurate matching with artery. Accurate matching is achieved by increasing and decreasing device circumference (C) while device is in the artery for direct comparison under X-Ray fluoroscopy.

Figures 10A, 10B, 11:
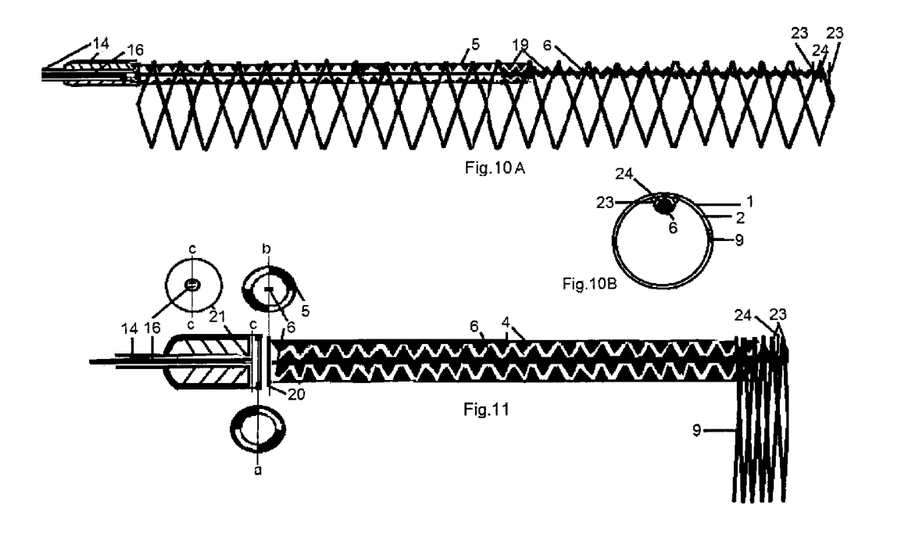
FIG. 10A shows male threads on a control wire at maximum disengagement with female threads in a control tube with a turning arm in a clamp tube having a clamp for gripping a clamp holder on the control tube and turning arm turning the control wire.
FIG. 10B is a cross sectional view of a distal hanger between the most distal of the connected outer and inner spirals and two flanges attached on threaded control wire on either side of the hanger that allow threaded control wire to turn in the distal hanger.
FIG. 11 shows male threads on a control wire having maximal overlap with female threads in a control tube with details of mechanism for turning threads on control wire and with distal end of double spiral stent attached to control tube implying presence of double spiral stent over entire control tube and attachment to control wire at proximal end.

FIG. 10A shows an alternative configuration in which control tube 5 and control wire 6 have male and female threads 19

(rather than indents detents 15) that are engaged. The proximal end of control tube 5 is connected to one or two turns of wire of the proximal end of spiral stent 9 and the distal end of control wire 6 is slidably connected to two turns of wire on the distal end of spiral stent 9 by means of two hangers 23 which surround control wire 6 and flange 24 attached to control wire 6 with hangers 23 on either side. There are no threads in the area between hangers 23 so control wire 6 rotates freely by hanging on hangers 23 while hangers 23 push or pull flange 24 in the proximal or distal direction as male and female threads on control wire 6 and control tube 5 engage and disengage to control length of spiral 9 (Ls) and thus circumference (C) of attached double spiral stent 9. The material of which control tube 5 and control wire 6 with threads 19 are made may be stainless steel or a nickel-titanium compound but heat treating is not utilized in manufacture as the resistance of threads 19 is sufficient to keep (male and female) threads 19 of control wire 6 and control tube 5 engaged. Turning control wire 6 in control tube 5 causes their overlap so no balloons are necessary to change the length of spiral stent 9 in this alternative configuration. The proximal end of control wire 6 is flattened to fit in a slot in turning arm 16 but this detail is better seen in FIG. 11. Turning arm 16 has a distal and proximal end with wire therebetween and is made in a circumference that slidably touches, but does not engage threads 19 of control tube 5 and thus is aligned with control wire 6 within control tube 5. Turning arm 16 is slotted on its distal end to fit together with the flattened proximal end of control wire 6 and is shown passing through control tube 5 for most of the length of control tube 5. This placement makes the overlap of control wire 6 and control tube 5 minimal and thus the length of attached spiral stent 9 maximum and circumference of spiral stent 9 minimum. Control tube 5 and control wire 6 are shown attached on the inner circumference of spiral stent 9 and if cover 8 is on spiral stent 9 it becomes stent graft 3.

FIG. 10B is a cross sectional view of the most distal of the turns of outer spiral 1 and inner spiral 2 that are parts of spiral stent 9. Hangers 23 show as a semicircle of wire, extending from circumference of most distal loops of wire of spiral stent 9 around distal end of control wire 6 and back to circumference of spiral stent 9 whereby hangers 23 enclose flange 24 near the distal end of control wire 5 which has no threads between hangers 23. This causes flange 23 to be pushed or pulled against hangers 23 as threaded control wire 5 is turned by turning arm 16 to be threaded deeper into or out of threaded control tube 6 thus causing attached said spiral stent 9 to increase or decrease in length (Ls) and thus circumference (C).

FIG. 11 shows control tube 5 and control wire 6 with threads 19 fully engaged and thus making length (Ls) of spiral stent 9 or double spiral 3 at the minimum and circumference (C) at the maximum. Spiral stent 9 is shown only near the distal end of control tube 5 and control wire 6 so as not to obscure the image with threads 19, but it should be understood that proximal end of spiral stent 9 is attached to proximal end of control tube 5 as shown in FIG. 10A, and flange 24 is attached to control wire 6 with hangers 23 on either side which are attached to most distal wire loops of spiral stent 9 as shown in FIG. 10A and in cross section in FIG. 10B. The detailed view in cross section b shows the flattened proximal end of control wire 6 that is engaged by the slotted distal end of turning arm 16 shown in cross section c. It was shown in FIG. 10 that turning arm 16 and control wire 6 are aligned so the slotted distal end of turning arm 16 and the flattened proximal end of control wire 6 engage in a manner that allows operator to turn turning arm 16 to cause control wire 6 to turn and thus cause threads 19 of control wire 6 and control tube 5 to engage and control length (Ls) and circumference (C). This detail view also shows clamp 21 on the distal end of clamp tube 14. Clamp tube 14 has a distal end and a proximal end with a tube therebetween of a size to slidably receive turning arm 16.

Clamp tube 14 and clamp 21 have turning arm 16 located inside. Clamp holder 20 is two quarter sections of a rim extending slightly larger than the circumference of control tube 5 at the proximal end of control tube 5. The quarter sections are best seen in cross section b. On the distal end of clamp 21 are two corresponding quarter sections of a rim that match the shape of the quarter sections of clamp holder 20. Clamp 21 and clamp holder 20 have their quarter sections aligned to pass each other and then turned a quarter turn their quarter sections are engaged in order to hold them together. To release them they are tuned a quarter turn in the opposite direction. In this way they can be clamped together while turning arm 16 turns control wire 6 and after operator is satisfied with the circumference of spiral stent 9 or stent graft 3, they are unclamped and clamp 21, and turning arm 16 are thus disengaged so they can be removed from the body along with guidewire 7. The disengagement leaves control tube 5, clamp holder 20, control wire 6 and spiral stent 9 or stent graft 3 free to remain in the artery with circumferences of spiral stent 9 matching the artery circumference. To ensure that the locking mechanism stays locked until the operator achieves the desired circumference, clamp 21 may be made in an alternative configuration of heat treated nickel titanium compound such that clamp 21 holds clamp holder 20 tightly until body heat is reached at which time clamp 21 expands to make its release easy. Balloons 10, 11 or 22 can be used with cooling fluid to control temperature of clamp 21. As another alternative configuration clamp 21 and clamp holder 20 may be supplied with simple threads to accomplish their engagement and heat treated nickel titanium compound used in a similar way to that described to ensure release when body temperature is reached.

The invention claimed is:

1. An intravascular system comprising: with a double spiral stent component, and kits of components as means for delivering and for increasing and decreasing length and circumference of said double spiral stent comprising
    a. an outer spiral having a distal end and a proximal end with a length of wire (Lw) therebetween wound in a clockwise direction in a circumference (C) and in a number of turns (N) and with a distance between said turns that results in a length of said outer spiral (Ls) between said distal end and said proximal end, and
    b. an inner spiral having a distal end and a proximal end with a length of wire (Lw) therebetween having dimensions approximately equal to those of said outer spiral with dimension differences that enable said inner spiral to be slidably located inside said outer spiral, with the length of wire of said inner spiral wound in a counter-clockwise direction in a circumference (C) and a number of turns (N) and with a distance between the turns that results in a length of spiral (Ls) between said distal end and said proximal end of said inner spiral which is the same as the length of said outer spiral (Ls) and,
    c. the distal ends of said outer spiral and said inner spiral being attached to each other and the proximal ends of said outer spiral and said inner spiral being attached to each other to produce said double spiral stent, and
    d. a distal balloon mounted on distal end of a distal catheter which has a proximal end, a distal end and a catheter body therebetween and said distal catheter being slidably received in a proximal catheter, and said distal and said distal catheter being configured with fluid lines and fluid ports to allow said distal balloon to be filled with chilled or normal inflation fluid, and said proximal catheter having a proximal end, a distal end and a catheter body there between being of a size to allow said distal catheter to be slidably received within said proximal catheter, and a proximal balloon mounted near said distal end of said proximal catheter, and said proximal catheter being configured with fluid lines and fluid ports to allow said proximal balloon to be filled with chilled or normal inflation fluid, whereby dimensions of said double spiral stent, are related according to the formula of $C=(Lw-Ls)/N$, wherein a maximum circumference of said double spiral stent is obtained when Ls is minimum because Lw and N remain the same regardless of said length (Ls) of said double spiral stent, and a minimum circumference is obtained when said length (Ls) is maximum and this is achieved by an operator making maximum a distance between said proximal balloon and said distal balloon while said double spiral stent is being delivered to its desired location in a vessel of the body because said proximal balloon and said distal balloon, are of a size such that when inflated to frictionally attach near said proximal end and said distal end of said double spiral stent and thus hold said double spiral stent at the maximum length and thus the minimum circumference, when operator chooses said length and when operator chooses to move said proximal and said distal catheters so as to bring said distal and said proximal balloons closer together, while adjusting inflation of said proximal and distal balloons sufficiently to maintain their frictional attachments to said spiral stent, and this causes said spiral stent to decrease in length and thus increase in circumference.

2. The device of claim 1 further including, a cover placed on said double spiral stent either between said outer spiral and said inner spiral or outside said outer spiral, whereby the double spiral stent is converted to a double spiral stent graft with said cover that is configured to resist growth of diseased plaque back through an uncovered portion of said double spiral stent.

3. The device of claim 1 further including, said outer spiral and said inner spiral being shaped with a taper by means of winding on a tapered mandrel configured to match the taper of an artery into which said double spiral stent is to be placed.

whereby a circumference of a taper of the double spiral stent is made by winding on a tapered mandrel to match taper of an artery.

4. The device of claim 1 further including, a. a control wire having a distal end and a proximal end with a wire therebetween with male threads being on said control wire, and said male threads being slidably received by female threads in a control tube, and said proximal end of said control wire is flattened and near said distal end of said control wire a flange is attached so as to be located between two hangers which are attached to distal-most turns of wire of said double spiral stent, and b. said control tube having a distal end and a proximal end with a tube therebetween being of a length equal to length of said control wire and of a circumference to slidably receive said control wire, and said proximal of said control tube end is attached to turns of wire on a proximal end of said double spiral, and said female threads being inside said control tube that match said male threads on said control wire and a clamp holder as a rim in quarter sections on said proximal end of said control tube, and c. a turning arm having a distal end and a proximal end and a flexible wire therebetween and a slot in said distal end of said flexible wire made to fit said flattened proximal end of said control wire, and d. a clamp tube having a proximal end, a distal end and therebetween a tube of a size to slidably receive said turning arm, and e. a clamp attached near said distal end of said clamp tube said clamp having quarter sections to match said quarter sections of said clamp holder with said clamp being of a size and configuration to hold and to release said clamp holder on said control tube by twisting said quarter sections of said clamp and said clamp holder to align or not align, whereby a combined length of said control tube and said control wire of this configuration will lock in place thus locking attached double spiral stent to a same length when a desired circumference of said double spiral is obtained by pushing said quarter sections of said clamp and said clamp holder past each other and twisted to engage allowing aligned said turning arm and said control wire to be engaged by said slot and said flattened end so turning said turning arm thus causes said male threads on said control wire to engage more or fewer of said female threads in said control tube causing the combined length of said control wire and said control tube to change in length (Ls) and thus causing circumference (C) to change accordingly and when said control wire is completely unscrewed from said control tube the length of said double spiral stent is about twice the length of control tube, thus changing the combined length of the control tube and control wire assembly compresses or stretches the length of the attached double spiral stent (Ls) and thus the circumference of the double spiral stent is changed according to the formula of $C=Lw-Ls/N$ and after desired circumference is obtained by engaging more or fewer threads, said clamp and said clamp holder are disconnected by turning them in opposite directions thus disengaging said control wire, control tube and spiral stent from said turning arm and said clamp.

5. The device of claim 1 further including, a. a control wire having a proximal end, a distal end and a wire therebetween having indents and detents on said control wire, and said proximal end being permanently attached to a proximal end of said double spiral stent, and said control wire being of a size such that said indents and detents slidably pass matching indents and detents in a control tube, and b. said control tube having a proximal end, a distal end and a tube there between having said indents and detents inside said control tube that match said indents and detents on said control wire, and said control tube being made of a nickel-titanium compound which is heat treated to decrease in size at body temperature, causing said indents and detents to engage, and said distal end of said control tube is permanently attached to a distal end of said double spiral stent, whereby components of this configuration for locking a desired circumference of said double spiral stent in place provide for said indents and said detents of said control wire and of said control tube that do not engage when below body temperature as said proximal balloon and said distal balloon are moved closer together or farther apart to change extent said control wire overlaps said control tube; operator places said proximal balloon at proximal end of said double spiral stent and said distal balloon at said distal end of said double spiral stent and inflates said balloons to grip said proximal and said distal ends of said double spiral stent, and operator moves said proximal and said distal catheters to impart movement through said proximal and said distal balloons to said double spiral stent thus changing its length (Ls) and circumference (C), as said distal balloon engages said distal end of said double spiral stent and said proximal balloon engages said proximal end of said double spiral stent and operator moves said distal catheter in said proximal catheter the length (Ls) of said double spiral stent is changed as is circumference (C), and chilled inflation fluid in said proximal and said distal balloons keeps said control wire and said control tube below body temperature until operator obtains a desired circumference whereupon operator removes chilled inflation fluid allowing body temperature to be obtained; at body temperature said control tube shrinks on said control wire causing said indents and detents to engage thus permanently locking said control wire and said control tube together at the desired length and thus circumference of said double spiral stent.

6. The device of claim 1 further including,
a. clips being circular loops of wire placed in horizontal and/or vertical orientations around one or more junctions where said length of wires of said outer spiral and said inner spiral cross, and
b. said clips being made of a nickel-titanium compound that is heat treated to shrink at body temperature,
whereby said clips when at body temperature which causes them to shrink on said junction where said outer spiral and said inner spiral cross cause said junction to be squeezed thus tending to prevent said junction from flexing away from a particular angle of said cross which is associated with, a particular length and circumference of said double spiral stent and when not shrunk said particular angle of said junctions on which one or more said clips are located flex as much as they flex without said clips being present and when said clips are heat treated and said clips reach body temperature said clips squeeze said junctions and prevent said particular angle from flexing and thus preventing change in said length and said circumference of said outer spiral and said inner spiral, and when clips are in both horizontal and vertical directions on a single junction, said junction is more resistant to flexing than when only one clip is on said single junction.

7. The device of claim 1 further including,
a. a cooling balloon mounted on said distal catheter, and
b. said distal catheter having said fluid lines and said fluid ports to provide chilled inflation fluid or normal inflation fluid to said cooling balloon,
whereby heat treated components in contact with said cooling balloon will retain their size and shape until cooling fluid is replaced by normal inflation fluid at which time body temperature causes heat treated components to go to their memory size and shapes.

\* \* \* \* \*